United States Patent

Takasu

[11] Patent Number: 5,190,518
[45] Date of Patent: Mar. 2, 1993

[54] SURGICAL DEVICE FOR THE TREATMENT OF HYPER HIDROSIS

[76] Inventor: Katsuya Takasu, 124-1, Aza-kamigochu, Oaza-akabane, Ishiki-cho, Hazu-gun, Aichi-ken, Japan

[21] Appl. No.: 681,267

[22] Filed: Apr. 8, 1991

[30] Foreign Application Priority Data

Oct. 12, 1990 [JP] Japan ................... 2-275014

[51] Int. Cl.⁵ .............................................. A61B 17/20
[52] U.S. Cl. ........................................ 604/22; 604/902
[58] Field of Search ............ 128/24 AA; 604/22, 902; 606/169

[56] References Cited

U.S. PATENT DOCUMENTS

| | | | |
|---|---|---|---|
| 4,428,748 | 1/1984 | Peyman et al. | 604/22 |
| 4,689,040 | 8/1987 | Thompson | 604/22 |
| 4,886,491 | 12/1989 | Parisi et al. | 604/22 |
| 4,982,730 | 1/1991 | Lewis, Jr. | 604/22 |
| 5,057,098 | 10/1991 | Zelman | 604/22 |

Primary Examiner—Stephen C. Pellegrino
Assistant Examiner—Michael Rafa
Attorney, Agent, or Firm—Armstrong, Westerman, Hattori, McLeland & Naughton

[57] ABSTRACT

A surgical device for hyper hidrosis featuring a pipe-portion having a suction opening on its upper surface, with a suction path inside of the pipe. The opening has a convex scraping portion at its front edge. A handle, in which the pipe portion is detachably installed, has a vibration generator for propagating ultrasonic vibrations to the pipe portion, and has a passage which connect to a suction pipe, and is connected to an ultrasonic generator which generates electrical energy which is changed to ultrasonic vibrations by the vibration generator in the handle. A suction portion, which has a vacuum pump is connected to the suction path through the suction pipe.

4 Claims, 3 Drawing Sheets

SURGICAL DEVICE FOR THE TREATMENT OF HYPER HIDROSIS

BACKGROUND OF THE INVENTION

1. Field of the Invention

The present invention is a surgical device for the treatment of hyper hidrosis. This condition is typically caused by excess sweat gland tissue in the affected area, and an accepted treatment is the surgical removal of the excess tissue.

2. Description of the Related Art

One available treatment for hyper hidrosis (Osmidrosis) is to surgically remove sweat gland tissue from an affected area, thereby reducing perspiration in the area. The prior art method of accomplishing this goal is to incise the skin of the affected area and remove the sweat gland tissue from the skin. In such a surgical operation, however, a large incision is required, which often leaves a large scar. Furthermore, the incision requires a lengthy and often painful recovery period.

SUMMARY OF THE INVENTION

The object of the present invention is to provide a new surgical device for the treatment of hyper hidrosis (Osmidrosis) which can remove the excessive sweat gland tissue effectively without requiring large incisions associated with standard surgical procedures. Another object of present invention is to provide a surgical device which can reduce the physical and mental suffering coincident with this type of treatment.

In order to achieve the object mentioned above, the present invention has been developed which is a surgical device for the treatment of hyper hidrosis, comprising a tip having a suction opening on uppersurface of a pipe with a suction path inside of the pipe, and has a convex scraping portion at a front end of the opening, a handle in which the tip is installed which has a vibration generator propagating ultrasonic vibrations to the tip, and which also has a passage which connects to a suction pipe. An ultrasonic generator is provided for the purpose of generating electrical energy which is changed to ultrasonic vibrations by the vibration generator of the handle. A suction device, which includes a vacuum pump is, connected with the passage through the suction pipe.

Another feature of the present invention as described above, is that the tip has the added feature of being removable from the handle.

Tip is inserted into the sweat gland tissue of the affected area through a small incision, about 5-10 mm, which is large enough to insert the head of the tip into the skin. The ultrasonic generator is then activated, and the ultrasonic vibrations are propagated through the vibration generator into the tip.

The tip vibrates at ultra high-speed, and with sufficient amplitude to crush the sweat gland tissue through the movement of the tip.

On the upper surface of the tip, there is a suction opening, and the tip includes a convex scraping portion on the front end of the opening, so that the tip can scrape and the crushed tissue carefully from under the skin by the ultra-high speed vibrattion, which is then drawn into the suction opening.

The suction path of the tip is connected with the passage in the handle, accordingly, the crushed tissue is drawn into the suction part with vacuum pump through the suction pipe which is connected to the passage.

BRIEF DESCRIPTION OF THE DRAWINGS

The above and other objects and the attendant advantages of the present invention will become readily apparent by reference to the following detailed description when considered in conjunction with the accompanying drawings wherein.

DETAILED DESCRIPTION OF EMBODIMENTS

Figure 1:
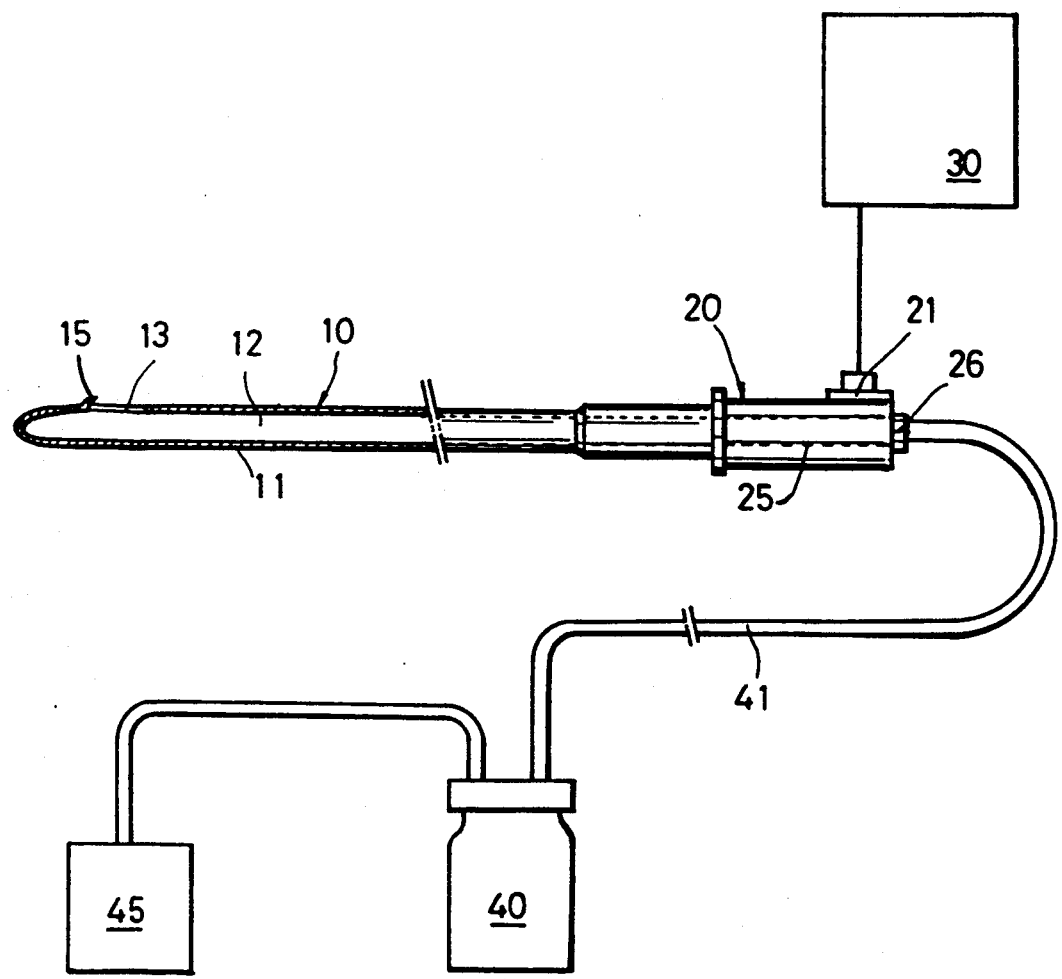
FIG. 1 is a partial cutaway view of a surgical system for hyper hidrosis according to the present invention.

FIG. 1 illustrates a surgical device for hyper hidrosis according to the present invention. The device includes tip 10, handle 20, ultrasonic generator 30 and suction part 40.

The tip is comprised of pipe-shaped part 11 which can be made of metal, one end of which tapers to a rounded point. The inner portion of pipe-shaped part 11 is a part of suction path 12 for absorbing crushed sweat gland tissue. A suction opening 13 is provided on upper surface of pipe-shaped part 11, and has a convex scraping portion 15 to scrape the crushed sweat gland tissue at the front edge of the opening. Convex scraping portion 15, shown in FIG. 1, is protrudent member having a small acute angle, and desireable height of the protrudent member is about 1 mm.

Figure 2:
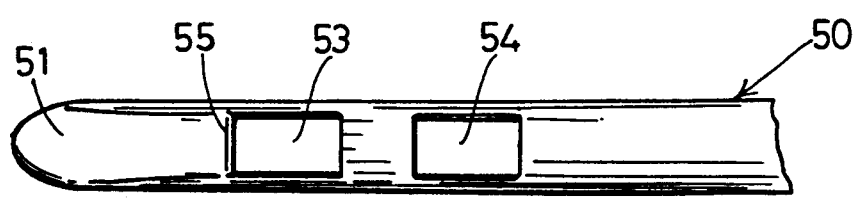
FIG. 2 is a plan view showing the features of the tip used for surgery according to the present invention.
Figure 3:
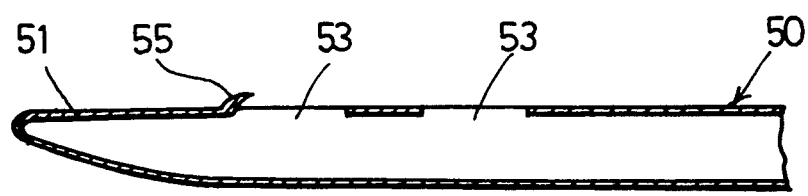
FIG. 3 is a sectional view shown in FIG. 2.

Furthermore, with reference to examples shown in FIG. 2, it is possible to have multiple suction openings in the tip. The tip 50, as shown in FIG. 2 and FIG. 3, has two suction openings 53, 54 adjacent to each other on an upper of pipe-shaped part 51. In this case, convex scraping portion 55 is attached to the front edge of the front suction opening.

Figure 4:
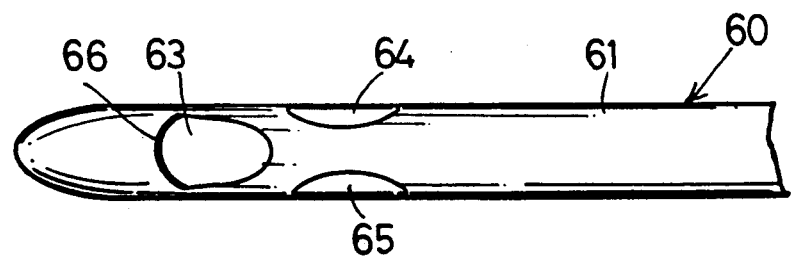
FIG. 4 is a plan view of a second embodiment of the tip according to the present invention.
Figure 5:
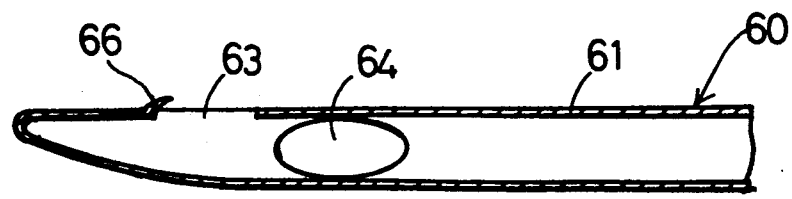
FIG. 5 is a sectional view of the tip shown in FIG. 4.

Also, the tip 60, shown in FIG. 4 and FIG. 5, has suction opening 63 on an upper surface of pipe-shaped part 61, and also has suction openings 64, 65 on both sides of the pipe-shaped part 61.

Handle 20 is intended to be held by an operator when the device is in use. The tip 10 is installed detachably in the handle 20, which has a vibration generator 21 and a passage 25. The vibration generator 21 propagates ultrasonic vibrations to tip 10 through handle 20. It is connected to the ultrasonic generator 30, and then converts the electrical energy into ultrasonic vibrations and propagates these vibrations to the tip 10.

A recommended frequency of the vibration generator according to the present invention is 2400 times per second or similar high frequency, with a 300 $\mu$m-maximum amplitude.

The passage 25 is connected to the suction path 12, and has connecting portion 26 to connect with a suction pipe 41 which is connected with the suction part 40.

One type of ultrasonic generator which can be used in the present invention can utilize an oscillation system with an electrostrictive transducer, PZT, with an osillation frequency of 24 KHZ, and ultrasonic generating power is 100 w-maximum.

Suction part 40 is connected with the passage 25 in the handle through suction pipe 41, and is connected to a vacuum pump, and takes in the crushed sweat gland tissue which is drawn into the suction opening part 13.

Figure 6:
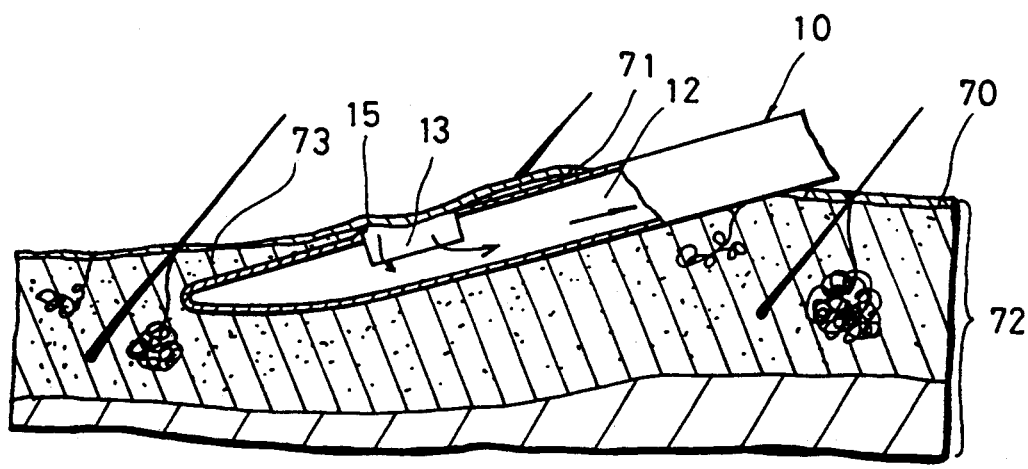
FIG. 6 is a sectional view of the surgical device of the present invention being used to remove sweat glands.

The use of invention will be described below with reference to FIG. 6;

A small incision is made in skin 70 which is the area sought to be treated; approximately 5-10 mm in length. The tip 10 is inserted into the hypodermic tissue 72 through incision. Hypodermic tissue 72 illustrates a typical hyper-hydrositic area, which has excess seat gland tissue 73 several millimeters thick causing hyper hidrosis.

Tip 10 is installed into the handle and vibration generator 21 connected to ultrasonic generator 30 with the ultrasonic generator functioning and propagating ultrasonic vebrations through the vibration generator.

Sweat gland tissue 73 is crushed by the ultrasonic vibrations of the tip 10 which is inserted into the hypodermic tissue 72. The crushed sweat gland tissue 73 is absorbed through suction opening 13 of tip 10 and the adhering tissue portion on the undersurface of the skin is scraped by convex scraping portion 15 on the front edge of the opening, and it is also drawn to the suction path 12 in the pipe-shaped part 11.

The tissue in the suction path 12 is drawn into the suction part 40 through the passage 25 in the handle and the suction pipe 41. A recommended suction pressure in the vacuum pump of the suction part is 650 mmHg-maximum pressure, which ensures that all of the crushed sweat gland tissue and blood is drawn into the suction part, without allowing blockage to form in the passage and suction pipe.

In a surgical operation for hyper hidrosis (Osmidrosis) in the prior art, usually, the skin of the affected area requires a large incision through which to remove unwanted tissue is removed. However, in the present invention, the skin only requires a small 5-10 mm incision therein. Therefore, the incision heals faster, and the surgical operation is more cosmetically acceptable because a large scar does not remain after the surgical operation.

A surgical operation according to the invention results in less physical trauma, so that physical and mental suffering of the patients is reduced. Therefore, the desirability and feasibility of surgical treatment of hyper hidrosis is increased by the advent of the present invention.

It is readily apparent that the above-described invention has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A surgical device for the treatment of hyper hidrosis, comprising:
    a pipe portion having an enclosed tip on one end thereof, said pipe portion having at least one flattened surface along an entire length thereof, and having a suction opening on an upper surface thereof;
    a convex scraping portion protruding outward from a front edge of the suction opening;
    a handle detachably connected to said pipe portion, and having a passage therethrough;
    vibration generator means for propagating ultrasonic vibrations to said pipe portion, said vibration generator means mounted on said handle;
    suction pipe means, connected to the passage of said handle;
    ultrasonic generator means for generating electrical energy to said vibration generator means;
    a suction means for providing suction, connected to said suction pipe means; wherein said vibration generator means propagates ultrasonic vibrations to said pipe portion by converting electrical energy provided by said ultrasonic generator means, a suction is provided to said suction opening by said suction means, through said suction pipe means, said handle, and said pipe portion.

2. A surgical device for the treatment of hyper hidrosis according to claim 1, wherein said pipe portion includes a plurality of suction openings on an upper surface thereof.

3. A surgical device for the treatment of hyper hidrosis according to claim 1, wherein said pipe portion further includes at least one suction opening on at least one lateral surface thereof.

4. A surgical device for the treatment of hyper hidrosis according to claim 2, wherein said pipe portion further includes at least one suction opening on at least one lateral surface thereof.

* * * * *